United States Patent [19]

Harada et al.

[11] Patent Number: 4,673,644
[45] Date of Patent: Jun. 16, 1987

[54] NOVEL STRAINS OF AGROBACTERIUM AND PREPARATION OF CYCLIC (1→2)-β-D-GLUCAN

[75] Inventors: Tokuya Harada, Toyonaka; Tadashi Higashiura, Ibaraki, both of Japan

[73] Assignee: Daikin Kogyo Co., Ltd., Osaka, Japan

[21] Appl. No.: 544,998

[22] Filed: Oct. 24, 1983

[30] Foreign Application Priority Data

Nov. 1, 1982 [JP] Japan ................... 57-193119

[51] Int. Cl.$^4$ ............ C12P 19/04; C12N 1/20; C12N 15/00
[52] U.S. Cl. ..................... 435/101; 435/253; 435/172.1
[58] Field of Search ............ 435/101, 253, 172.1, 435/819

[56] References Cited

U.S. PATENT DOCUMENTS 4,355,106  10/1982  Lawford .............. 435/819

FOREIGN PATENT DOCUMENTS 0106311  4/1984  European Pat. Off. ........... 435/101

OTHER PUBLICATIONS

Hisamatsu, M., *J. Gen. Microbiol.*, vol. 128, pp. 1873–1879, 1982.

"XIth International Carbohydrate Symposium", Aug. 22–28, 1982, (Abstract III–61).

*Primary Examiner*—Thomas G. Wiseman
*Assistant Examiner*—Jayme A. Huleatt
*Attorney, Agent, or Firm*—Birch, Stewart, Kolasch & Birch

[57] ABSTRACT

A novel strain belonging to the genus Agrobacterium, which does not produce acidic extracellular polysaccharides or their constituents and/or water-insoluble extracellular polysaccharides, and which produces cyclic β-1,2-glucan.

14 Claims, 1 Drawing Figure

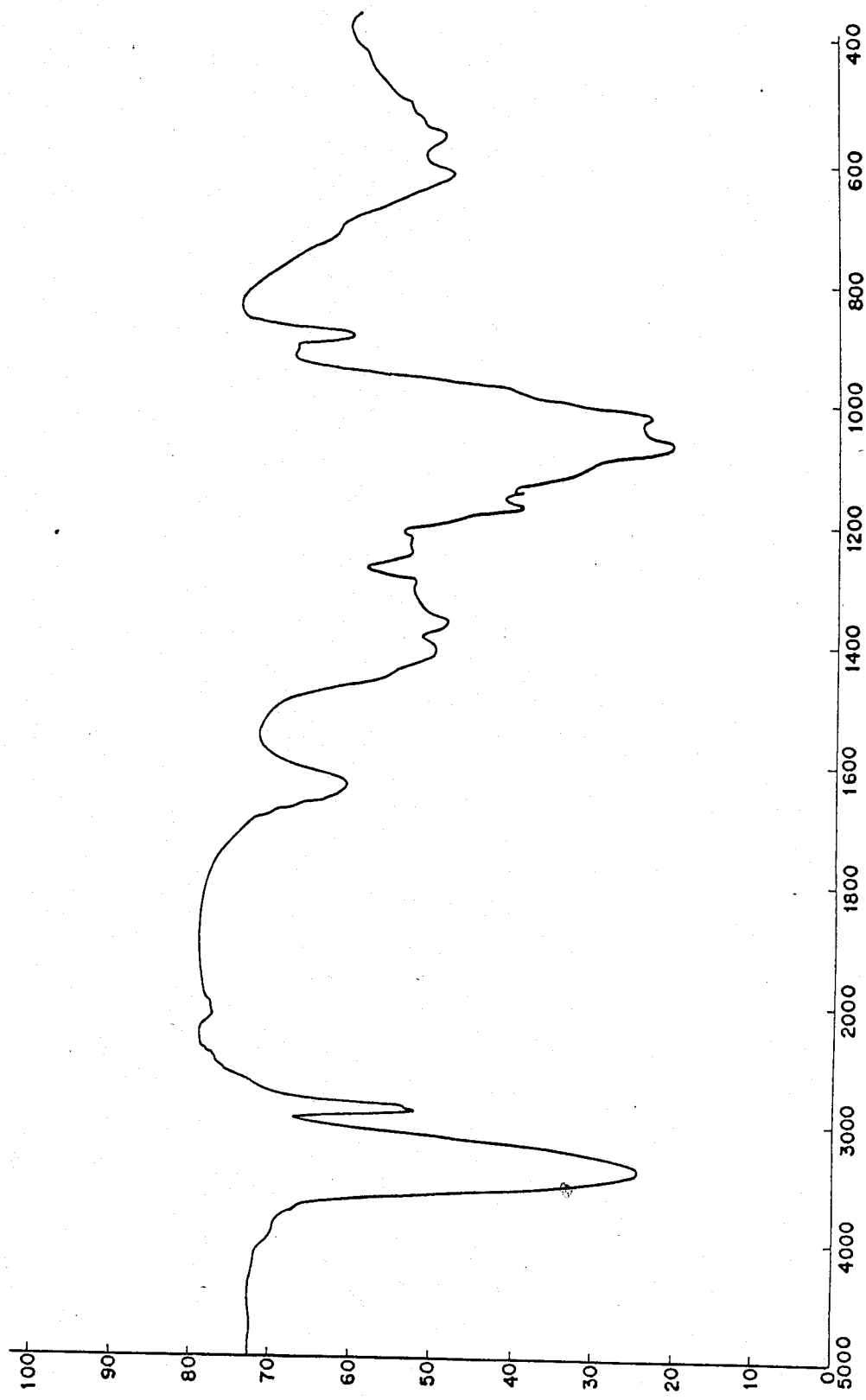

NOVEL STRAINS OF AGROBACTERIUM AND PREPARATION OF CYCLIC (1→2)-β-D-GLUCAN

The present invention relates to novel strains belonging to genus Agrobacterium and the preparation of cyclic (1→2)-β-D-glucan (hereinafter referred to as cyclic β-1,2-glucan) by the use of said novel strains. More particularly, it relates to novel variant strains belonging to the genus Agrobacterium and a process for preparing cyclic β-1,2-glucan by the use of said novel variant strains.

It is known that cyclic β-1,2-glucan improves the growth of root nodule of plants (cf. Plant and Soil, 64 (3), 315-324). Cyclic β-1,2-glucan may be used, like cyclodextrin, to produce clathrate compounds It is also known that strains belonging to the genus Agrobacterium produce cyclic β-1,2-glucan (cf. J. Biol. Chem., 143, 491 (1942), J. Am. Chem. Soc., 72, 5024 (1950) and Carbohydrate Research, 82, 366 (1980)).

However, the known strains belonging to genus Agrobacterium show low productivity of cyclic β-1,2-glucan and produce simultaneously acidic extracellular polysaccharides, which increase viscosity of a culture medium and make the cultivation of the strain difficult due to foaming under aeration.

As a result of the extensive study of the production of cyclic β-1,2-glucan by the use of strains belonging to the genus Agrobacterium, it has now been found that certain specific variant strains belonging to the genus Agrobacterium have high productivity of cyclic β-1,2-glucan and do not produce the acidic extracellular polysaccharides (e.g., succinoglycan) or their constituents (e.g., the octasaccharide repeating units thereof) and/or water-insoluble extracellular polysaccharides (e.g., curdlan).

According to the present invention, there is provided a novel strain belonging to genus Agrobacterium which does not produce acidic extracellular polysaccharides or their constituents and/or water-insoluble extracellular polysaccharides.

Typical strains of the invention are *Agrobacterium radiobacter* Al-5 (FERM BP-373), *Agrobacterium radiobacter* Al-7 (FERM BP-378) and *Agrobacterium radiobacter* A-12 (FERM BP-377). All of them were obtained by mutating a known strain, *Agrobacterium radiobacter* IFO12665, and deposited at Fermentation Research Institute, Agency of Industrial Science and Technology in Japan under the Budapest Treaty under the deposition numbers as described above.

The taxonomical characteristics of these strains are the same as those of *Agrobacterium radiobacter* IFO12665 except that the strains of the invention do not produce the acidic extracellular polysaccharides and/or the water-insoluble extracellular polysaccharides.

The mutation of the strain can be carried out by per se conventional methods, for example, by irradiation of UV light or high energy radiation or by the treatment with chemicals (eg. N-methyl-N'-nitro-N'-mitrosoguanidine). The mutated strains are cultivated on an agar plate culture medium, and from grown colonies, comparatively small ones having non-glossy surfaces are selected, thereby strains which do not produce the acidic extracellular polysaccharides and/or the water-insoluble extracellular polysaccharides are obtained.

According to the invention, cyclic β-1,2-glucan is prepared by cultivating the strain of the invention in a culture medium to produce cyclic β-1,2-glucan in the culture medium and recovering produced cyclic β-1,2-glucan from the culture medium.

The culture medium contains carbon sources which can be utilized by the strains (eg. glucose, mannitol, sucrose, molasses, etc.), nitrogen sources which can be metabolized by the strains (eg. yeast extract, peptone, corn steep liquor, ammonia, ammonium sulfate, ammonium nitrate, etc.) and various inorganic salts which are essential to the growth of the strains.

The strain is usually cultivated under an aerobic condition, for example, by shaking culture or submerged culture under aeration at a temperature of from 20° to 40° C., preferably from 25° to 35° C., particularly at about 30° C. During the cultivation, pH of the culture medium is adjusted with a suitable acid or base such as sulfuric acid or sodium hydroxide to 5 to 8, preferably 6.5 to 7.5, particularly about 7.2. The cultivation time is at least 24 hours. Preferably, in the case of shaking culture, it is from 3 to 10 days and in the case of submerged culture under aeration by means of, for example, a jar fermenter, it is from 3 to 7 days. Under these cultivation conditions, cyclic β-1,2-glucan is produced in a high yield.

After the cultivation of the strain, the strain cells are removed from the culture medium by a per se conventional method such as centrifugation, and the medium is concentrated. Then, an organic liquid such as ethanol is added in the medium and again centrifuged to remove the residual strain cells and polysaccharides contained in the medium. By the addition of the organic liquid in the supernatant liquid, crude cyclic β-1,2-glucan is precipitated. The crude cyclic β-1,2-glucan can be purified by a per se conventional method, for example, gel filtration.

As described above, since the novel variant strains belonging to genus Agrobacterium of the invention do not produce any acidic extracellular polysaccharide or any water-insoluble extracellular polysaccharide, the viscosity of the culture medium does not increase, and the culture medium is hardly foamed under aeration. Therefore, the strains of the invention is effectively cultivated.

The present invention will be hereinafter explained further in detail by the following Examples.

EXAMPLE 1

*Agrobacterium radiobacter* IFO12665 was cultivated in the YPG culture medium containing yeast extract (1 g/dl), peptone (1 g/dl) and glucose (2 g/dl) at 30° C. for 24 to 48 hours and then suspended in 0.05M tris-maleate buffer solution (pH 6.0) containing N-methyl-N'-nitro-N'-nitrosoguanidine (200 μg/ml) in concentration of $10^5$ to $10^7$ cells/ml. The suspension was shaken at 30° C. for 30 minutes and centrifuged at 10,000 rpm for 5 minutes to recover the strain cells, which were suspended in physiological saline solution. The strain cells were washed with physiological saline solution twice and suspended in physiological saline solution in concentration of about $10^3$ to $10^4$ cells/ml.

The thus prepared suspension (0.1 ml) was spread on an agar plate culture (glucose, 2 g/dl; NH$_4$Cl, 0.2 g/dl; KH$_2$PO$_4$, 0.21 g/dl; Na$_2$HPO$_4$.12H$_2$O, 1.2 g/dl; MgSO$_4$.7H$_2$O, 0.03 g/dl; Na$_2$SO$_4$, 0.05 g/dl; yeast extract, 0.1 g/dl and agar, 2 g/dl) and cultivated at 30° C. for 3 to 4 days. From the grown colonies, a comparatively small one having non-glossy surface was selected to obtain a strain which does not produce any acidic extracellular polysaccharide, which is named *Agrobacterium radiobacter* Al-5 (FERM BP-373).

EXAMPLES 2 AND 3

In the same manner as in Example 1, *Agrobacterium radiobacter* Al-7 (FERM BP-378) and *Agrobacterium radiobacter* A-12 (FERM BP-377) were obtained.

EXAMPLE 4

In distilled water (1 l), glucose (40 g), $(NH_4)_2HPO_4$ (1.5 g), $KH_2PO_4$ (1.0 g), $MgSO_4.7H_2O$ (0.5 g), NaCl (10 mg), $CaCl_2$ (10 mg), $MnCl_2.4H_2O$ (10 mg), $CuSO_4.5H_2O$ (50 μg), $Na_2MOO_4.2H_2O$ (20 μg), $H_3BO_4$ (10 μg) and $CaCO_3$ (5 g) were added to prepare a culture medium. The culture medium (100 ml) was adjusted to pH of 7.2 with 1N sulfuric acid or 1N sodium hydroxide and then charged in 500 ml Erlenmeyer flask and sterilized.

*Agrobacterium radiobacter* Al-5 which had been prefermented in the culture medium as prepared above was inoculated in the same culture medium and cultivated at 30° C. with rotation at 220 rpm.

In the course of the cultivation, the viscosity of the medium did not increase even at the final stage of cultivation and the medium was flowable and foamed slightly.

After cultivation for 6 days, acetone (150 ml) was added in the medium and centrifuged at 5,000 rpm for 5 minutes. The supernatant was concentrated to 30 ml. In the concentrated supernatant, ethanol (60 ml) was added and again centrifuged at 10,000 rpm for 5 minutes to precipitate the residual strain cells and polysaccharides. From the supernatant, powdery or fibrous white crude cyclic β-1,2-glucan was precipitated by the addition of ethanol (360 ml), which crude product was collected by centrifugation at 10,000 rpm for 15 minutes. The collected product was washed with ethanol twice and dried under reduced pressure at 40° C. to obtain crude cyclic β-1,2-glucan (303.8 mg). The weight of the dried cells was 130 mg.

The crude product was developed on Sephadex (trade mark) G-25 column (diameter, 26 mm; length, 500 mm) with pure water to obtain a fraction (110 ml) containing cyclic β-1,2-glucan. The fraction was concentrated to 10 ml. In the concentrate, ethanol (100 ml) was added to precipitate powdery white cyclic β-1,2-glucan, which was recovered by centrifugation at 10,000 rpm for 15 minutes. The product was washed with ethanol twice and dried under reduced pressure at 40° C. to obtain pure cyclic β-1,2-glucan (235.3 mg). Infrared spectrum of the product is shown in the FIGURE of the drawings.

$^{13}$C-NMR: $\delta$ = 102.8, 102.6, 83.3, 82.6, 77.1, 76.3, 69.6 and 61.5 ppm (internal standard; dioxane).

A part of the thus obtained product was hydrolyzed by a per se conventional method. A part of the hydrolized product was analyzed by paper chromatography, and the other part was alditol-acetated and analyzed by gas chromatography. In both cases, only glucose was found. The angle of rotaion of the obtained product was $-5°$. Further, the obtained product was methylated, hydrolyzed and alditolacetated, and then analyzed by GC-MS, and it was found from the results that 1- and 2-positions of glucose participated in the bonding of cyclic β-1,2-glucan.

EXAMPLE 5

In the same manner as in Example 4 but using *Agrobacterium radiobacter* Al-7 in place of *Agrobacterium radiobacter* Al-5, cyclic β-1,2-glucan (200.2 mg) was obtained. The weight of the dried cells was 101 mg.

EXAMPLE 6

In the same manner as in Example 4 but using *Agrobacterium radiobacter* A-12 in place of *Agrobacterium radiobacter* Al-5, cyclic β-1,2-glucan (212.0 mg) was obtained. The weight of the dried cells was 125 mg.

COMPARATIVE EXAMPLE 1

In the same manner as in Example 4 but using *Agrobacterium radiobacter* IFO12665 in place of *Agrobacterium radiobacter* Al-5, cyclic β-1,2-glucan (156.5 g) was obtained. The weight of the dried cells was 104 mg.

In this cultivation, the viscosity of the medium increased at the final stage and the flowability of the whole medium deteriorated.

What is claimed is:

1. A novel strain belonging to the genus Agrobacterium, which produces cyclic β-1,2-glucan and which does not produce acidic extracellular polysaccharides, octasaccharide repeating units thereof and extracellular polysaccharides, wherein said strain is obtained by mutating *Agrobacterium radiobacter* IFO12665.

2. A novel strain according to claim 1, which is *Acrobacterium radiobacter* Al-5 (FERM BP-373).

3. A novel strain according to claim 1, which is *Agrobacterium radiobacter* Al-7 (FERM BP-378).

4. A novel strain according to claim 1, which is *Agrobacterium radiobacter* A-12 (FERM BP-377).

5. A process for preparing cyclic β-1,2-glucan, which comprises: cultivating a novel strain belonging to the genus Agrobacterium which produces cyclic β-1,2-glucan and which does not produce acidic extracellular polysaccharides, octasaccharide repeating units thereof and water-insoluble extracellular polysaccharides, in a culture medium to produce cyclic β-1,2-glucan in the culture medium; wherein said strain is obtained by mutating *Agrobacterium radiobacter* IFO12665 and recovering produced cyclic β-1,2-glucan from the culture medium.

6. A process according to claim 5, wherein the strain is *Agrobacterium radiobacter* Al-5 (FERM BP-373).

7. A process according to claim 5, wherein the strain is *Agrobacterium radiobacter* Al-7 (FERM BP-378).

8. A process according to claim 5, wherein the strain is *Agrobacterium radiobacter* A-12 (FERM BP-377).

9. A process according to claim 5, wherein the strain is cultivated at a cultivation temperature of from 20° to 40° C.

10. A process according to claim 5, wherein the pH of the culture medium is from 5 to 8.

11. A process according to claim 5, wherein the strain is cultivated at a cultivation time of at least 24 hours.

12. A novel strain belonging to the genus Agrobacterium, which produces cyclic β-1,2glucan and, which does not produce acidic extracellular polysaccharides, octrasaccharide repeating units thereof and water-insoluble extracellular polysaccharides which increase the viscosity of a sterile liquid culture medium containing one liter of water, glucose (40 g), $(NH_4)_2\text{-}HPO_4$ (1.5 g), $KH_2PO_4$ (1.0 g), $MgSO_4.7H_2O$ (0.5 g), NaCl (10 mg), $CaCl_2$ (10 mg), $MnCl_2.4H_2O$ (10 mg), $CuSO_4.5H_2O$ (50 μg), $Na_2MoO_4.2H_2O$ (20 μg), $H_3BO_4$ (10 μg)

and CaCO$_3$ (5 g) having a pH of 7.2 upon culturing said strain in said culture medium at 30° C. for a period of six days, wherein said strain is obtained by mutating *Agrobacterium radiobacter* IFO12665.

13. A novel strain belonging to the genus Agrobacterium, which produces cyclic β-1,2-glucan and which does not produce succinoglycan, octasaccharide repeating units thereof and curdlan which increase the viscosity of a culture medium upon culture at 30° C. for six days wherein said strain is obtained by mutating *Agrobacterium radiobacter* IFO12665.

14. A process for preparing cyclic β-1,2-glucan, which comprises: cultivating the strain according to claim 13 in a culture medium to produce cyclic β-1,2-glucan in the culture medium; and recovering produced cyclic β-1,2-glucan from the culture medium.

* * * * *